US008980573B2

(12) United States Patent
Rollinger et al.

(10) Patent No.: US 8,980,573 B2
(45) Date of Patent: Mar. 17, 2015

(54) METHOD FOR PROVIDING DIAGNOSIS OF CANCER USING SEPRASE AS A MARKER (75) Inventors: Wolfgang Rollinger, Polling (DE); Johann Karl, Peissenberg (DE); Jarema Peter Kochan, Towaco, NJ (US); Markus Roessler, Germering (DE); Michael Tacke, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 597 days.

(21) Appl. No.: 12/791,946

(22) Filed: Jun. 2, 2010

(65) Prior Publication Data
US 2010/0240081 A1  Sep. 23, 2010

Related U.S. Application Data (63) Continuation of application No. PCT/EP2008/010385, filed on Dec. 8, 2008.

(30) Foreign Application Priority Data

Dec. 10, 2007 (EP) .................................... 07023897
Aug. 29, 2008 (EP) .................................... 08015310

(51) Int. Cl.
*C12Q 1/37* (2006.01)
*G01N 33/574* (2006.01)

(52) U.S. Cl.
CPC .... *G01N 33/57423* (2013.01); *G01N 33/57407* (2013.01); *G01N 33/57419* (2013.01); *G01N 33/57473* (2013.01); *G01N 2333/96411* (2013.01)
USPC .......................................................... 435/23

(58) Field of Classification Search
None
See application file for complete search history.

(56) References Cited

FOREIGN PATENT DOCUMENTS

| EP | 0953639 A1 | 11/1999 |
|---|---|---|
| WO | 2005/043121 A3 | 5/2005 |
| WO | 2007/001420 A3 | 1/2007 |
| WO | 2007/085895 A3 | 8/2007 |
| WO | 2007/100374 A3 | 9/2007 |

OTHER PUBLICATIONS

Ariga et al., Int. J. Cancer, 95: 67-72, 2001.*
Zhang et al., PNAS 105: 13033-13038, 2008.*
Meyer et al., Clin. Cancer Res. 15: 2703-2710, 2009.*
Iwasa, Satoshi et al., "Increased expression of seprase, a membrane-type serine protease, is associated with lymph node metastasis in human colorectal cancer," Cancer Letters, 2003, pp. 91-98, vol. 199.
Zhang, Meng-zhen et al., "Expression of seprase in effusions from patients with epithelial ovarian carcinoma and its prognostic significance," Chinese Journal of Practical Gynecology and Obstetrics, 2007, pp. 268-270, vol. 23, English abstract.
Zhang, Xue-feng et al., "Relationship Between Expression of Seprase and Clinicopathological Characteristics in Colorectal Cancer," Chin J Bases Clin General Surg, 2006, pp. 89-93, vol. 13, No. 1, English abstract.
European Search Report issued May 6, 2008 in European Application No. 07023897.7.
International Search Report issued Mar. 31, 2009 in PCT Application No. PCT/EP2008/010385.
International Preliminary Report on Patentability issued Nov. 30, 2009 in PCT Application No. PCT/EP2008/013085.
Breiman, Leo, Random Forests, Machine Learning, 2001, pp. 5-32, vol. 45.
Buccheri, Gianfranco and Ferrigno, Domenico, Identifying Patients at Risk of Early Postoperative Recurrence of Lung Cancer: A New Use of the Old CEA Test, Annuals of Thoracic Surgery, 2003, pp. 973-980, vol. 75.
Duffy, M. J., Clinical Uses of Tumor Markers: A Critical Review, Critical Reviews in Clinical Laboratory Sciences, 2001, pp. 225-262, vol. 38, No. 3.
Friedman, Jerome H., Regularized Discriminant Analysis, Journal of the American Statistical Association, Mar. 1989, pp. 165-175, vol. 84, No. 405.
Fukasawa, Toshio et al., Clinical Evaluation of Serum NSE and CEA in Primary Lung Cancer Patients, Japanese Journal of Cancer Chemotherapy, May 1986, pp. 1862-1867, vol. 13, No. 5.
Ge, Yun et al., Fibroblast activation protein (FAP) is upregulated in myelomatous bone and supports myeloma cell survival, British Journal of Haematology, Apr. 2006, pp. 83-92, vol. 133, No. 1.
Goldstein, Leslie A. et al., Molecular cloning of seprase: a serine integral membrane protease from human melanoma, Biochimica et Biophysica Acta, 1997, pp. 11-19, vol. 1361.
Henry, Leonard R. et al., Clinical Implications of Fibroblast Activation Protein in Patients with Colon Cancer, Clinical Cancer Research, Mar. 15, 2007, pp. 1736-1741, vol. 13, No. 6.

(Continued)

*Primary Examiner* — Gyan Chandra
(74) *Attorney, Agent, or Firm* — Stinson Leonard Street LLP (57) ABSTRACT The present invention relates to a method aiding in the assessment of cancer. It discloses the use of the human fibroblast activation protein (FAP/seprase) as a universal marker of different cancer types. Seprase aids in the assessment of pulmonary or lung cancer (LC) or of colon cancer, e.g., of non-small cell lung carcinoma (NSCLC) or colorectal cancer (CRC), but also likely of other specific types of cancer. Such specific cancer types are, e.g., esophagus, head and neck cancer, stomach cancer, bile duct cancer, pancreas cancer, kidney cancer, cervix cancer, ovary cancer, breast cancer, bladder cancer, endometrium cancer or prostate cancer. Furthermore, it especially relates to a method for assessing cancer from a liquid sample, derived from an individual by measuring seprase in said sample. Measurement of seprase can, e.g., be used in the early detection of cancer or in the surveillance of patients who undergo surgery.

15 Claims, 2 Drawing Sheets (56) References Cited

OTHER PUBLICATIONS

Iwasa, Satoshi et al., 'Increased expression of seprase, a membrane-type serine protease, is associated with lymph node metastasis in human colorectal cancer', Cancer Letters, Sep. 28, 2005, pp. 229-236, vol. 227, No. 2.

Lee, Kyung N. et al., A novel plasma proteinase potentiates α2-antiplasmin inhibition of fibrin digestion, Blood, May 15, 2004, pp. 3783-3788, vol. 103, No. 10.

Lee, Kyung N. et al., Antiplasmin-cleaving enzyme is a soluble form of fibroblast activation protein, Blood, Feb. 15, 2006, pp. 1397-1404, vol. 107, No. 4.

Merle, P. et al., Early CYFRA 21-1 variation predicts tumor response to chemotherapy and survival in locally advanced non-small cell lung cancer patients, The International Journal of Biological Markers, pp. 310-315, vol. 19, No. 4, 2004.

Miller, M. R. et al., Standardisation of spirometry, European Respiratory Journal, 2005, pp. 319-338, vol. 26, No. 2.

Molina, R. et al., Tumor Markers (CEA, CA 125, CYFRA 21-1, SCC and NSE) in Patients with Non-Small Cell Lung Cancer as an Aid in Histological Diagnosis and Prognosis, Tumor Biology, 2003, pp. 209-218, vol. 24.

Parks, John E. et al., Fibroblast Activation Protein, a Dual Specificity Serine Protease Expressed in Reactive Human Tumor Stromal Fibroblasts, The Journal of Biological Chemistry, Dec. 17, 1999, pp. 36505-36512, vol. 274, No. 51.

Pineiro-Sanchez, Mayra L. et al., Identification of the 170-kDa Melanoma Membrane-bound Gelatinase (Seprase) as a Serine Integral Membrane Protease, The Journal of Biological Chemistry, Mar. 21, 1997, pp. 7595-7601, vol. 272, No. 12.

Ruczinski, Ingo et al., Logic Regression, 2003, Journal of Computational and Graphical Statistics, pp. 475-511, vol. 12, No. 3.

Scanlan, Matthew J. et al., Molecular cloning of fibroblast activation protein α, a member of the serine protease family selectively expressed in stromal fibroblasts of epithelial cancers, Proceedings of the National Academy of Sciences USA, Jun. 1994, pp. 5657-5661, vol. 91.

Schneider, Joachim et al., Fuzzy logic-based tumor-marker profiles improved sensitivity in the diagnosis of lung cancer, International Journal of Clinical Oncology, 2002, pp. 145-151, vol. 7.

Tijssen, P., Practice and Theory of Enzyme Immunoassays, 1985, pp. 43-78 and 108-115, Elsevier Science Publishers B. V., Amsterdam, The Netherlands.

Wagner, Henry, Jr., Postoperative Adjuvant Therapy for Patients With Resected Non-Small Cell Lung Cancer: Still Controversial After all These Years, Chest, 2000, pp. 110-118, vol. 117.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

\* cited by examiner

SEQ ID NO: 1

MKTPWKVLLG LLGAAALVTI ITVPVVLLNK GTDDATADSR KTYTLTDYLK

NTYRLKLYSL RWISDHEYLY KQENNILVFN AEYGNSSVFL ENSTFDEFGH

SINDYSISPD GQFILLEYNY VKQWRHSYTA SYDIYDLNKR QLITEERIPN

NTQWVTWSPV GHKLAYVWNN DIYVKIEPNL PSYRITWTGK EDIIYNGITD

WVYEEEVFSA YSALWWSPNG TFLAYAQFND TEVPLIEYSF YSDESLQYPK

TVRVPYPKAG AVNPTVKFFV VNTDSLSSVT NATSIQITAP ASMLIGDHYL

CDVTWATQER ISLQWLRRIQ NYSVMDICDY DESSGRWNCL VARQHIEMST

TGWVGRFRPS EPHFTLDGNS FYKIISNEEG YRHICYFQID KKDCTFITKG

TWEVIGIEAL TSDYLYYISN EYKGMPGGRN LYKIQLSDYT KVTCLSCELN

PERCQYYSVS FSKEAKYYQL RCSGPGLPLY TLHSSVNDKG LRVLEDNSAL

DKMLQNVQMP SKKLDFIILN ETKFWYQMIL PPHFDKSKKY PLLLDVYAGP

CSQKADTVFR LNWATYLAST ENIIVASFDG RGSGYQGDKI MHAINRRLGT

FEVEDQIEAA RQFSKMGFVD NKRIAIWGWS YGGYVTSMVL GSGSGVFKCG

IAVAPVSRWE YYDSVYTERY MGLPTPEDNL DHYRNSTVMS RAENFKQVEY

LLIHGTADDN VHFQQSAQIS KALVDVGVDF QAMWYTDEDH GIASSTAHQH

IYTHMSHFIK QCFSLP

METHOD FOR PROVIDING DIAGNOSIS OF CANCER USING SEPRASE AS A MARKER

RELATED APPLICATIONS

This application is a continuation of PCT/EP2008/010385 filed Dec. 8, 2008, which claims priority to European application EP 07023897.7 filed Dec. 10, 2007.

SEQUENCE LISTING

The instant application contains a Sequence Listing which has been submitted via EFS-Web and is hereby incorporated by reference in its entirety. Said ASCII copy, created on May 26, 2010, is named 24551US.txt and is 6,997 bytes in size.

FIELD OF THE INVENTION

The present invention relates to a method aiding in the assessment of cancer. It discloses the use of the human fibroblast activation protein (FAP/seprase) as a universal marker of different cancer types. Seprase aids in the assessment of pulmonary or lung cancer (LC) or of colon cancer, e.g., of non-small cell lung carcinoma (NSCLC) or colorectal cancer (CRC), but also likely of other specific types of cancer. Such specific cancer types are, e.g., esophagus, head and neck cancer, stomach cancer, bile duct cancer, pancreas cancer, kidney cancer, cervix cancer, ovary cancer, breast cancer, bladder cancer, endometrium cancer or prostate cancer. Furthermore, it especially relates to a method for assessing cancer from a liquid sample, derived from an individual by measuring seprase in said sample. Measurement of seprase can, e.g., be used in the early detection of cancer or in the surveillance of patients who undergo surgery.

BACKGROUND

Cancer remains a major public health challenge despite progress in detection and therapy. Cancer cells are characterized by the production of cancer-associated marker proteins. Cancer-associated proteins are found both in the tissues and in the bodily fluids of an individual who carries cancer cells. Their levels usually are low at the early stages of the carcinogenic progress and increase during the disease's progression and only in rare cases proteins are observed showing a decreased level in the course of disease progression. The sensitive detection of these proteins is an advantageous and promising approach for the diagnosis of cancer, in particular in an early stage diagnosis of cancer. The most prevalent cancer types are breast cancer (BC), lung cancer (LC) and colorectal cancer (CRC).

The most important therapeutic approaches for solid tumors are:
 a) surgical resection of the tumor,
 b) chemotherapy,
 c) treatment with biologicals, like anti-tumor antibodies or anti-angiogenic antibodies and
 d) a combination of the above methods.

Surgical resection of the tumors is widely accepted as a first line treatment for early stage solid tumors. Most cancers, however, are detected only when they become symptomatic, i.e., when patients already are in a rather late stage of disease progression.

The staging of cancer is the classification of the disease in terms of extent, progression, and severity. It groups cancer patients so that generalizations can be made about prognosis and the choice of therapy.

The different stages of CRC used to be classified according to Dukes' stages A to D. Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), Sobin, L. H., Wittekind, Ch. (eds): TNM Classification of Malignant Tumours, sixth edition, 2002). Once the TNM status is determined the patients are grouped into disease stages that are denoted by Roman numerals ranging form I to IV with IV being the most advanced disease stage. TNM staging and UICC disease stages correspond to each other as shown in the following Table taken from Sobin L. H. and Wittekind (eds.) supra.

| Interrelation of TNM staging and UICC disease stages | | | |
|---|---|---|---|
| UICC disease stage | T staging | N staging | M staging |
| Stage 0 | Tis | N0 | M0 |
| Stage I | T1, T2 | N0 | M0 |
| Stage IIA | T3 | N0 | M0 |
| Stage IIB | T4 | N0 | M0 |
| Stage IIIA | T1, T2 | N1 | M0 |
| Stage IIIB | T3, T4 | N1 | M0 |
| Stage IIIC | Any T | N2 | M0 |
| Stage IV | Any T | Any N | M1 |

What is especially important is, that early diagnosis cancer, e.g., of CRC translates to a much better prognosis. In CRC malignant tumors of the colorectum arise from benign tumors, i.e., from adenoma. Therefore, best prognosis have those patients diagnosed at the adenoma stage. Patients diagnosed as early as in stage $T_{is}$, N0, M0 or T1-3; N0; M0, if treated properly have a more than 90% chance of survival 5 years after diagnosis as compared to a 5-years survival rate of only 10% for patients diagnosed when distant metastases are already present.

Current detection methods including imaging methods, such as x-ray or nuclear resonance imaging in theory might at least partially be appropriate for use as a general screening tool. However, they are very costly and not affordable to health care systems for a general and broad use in mass screenings of large numbers of subjects, particularly for subjects without any tumor symptoms.

Thus, it is an object of the present invention to provide a simple and cost-efficient procedure of tumor assessments, e.g., to identify individuals suspect of having cancer. For this purpose, a general tumor marker which is detectable in body fluids, e.g., blood or serum or plasma or a panel of such markers, would be desirable.

A number of serum tumor markers are already in clinical use. For example the soluble 30 kDa fragment of cytoceratin 19 (CYFRA 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor and Diagnose (2000) TH Books Verlagsgesellschaft, Frankfurt/Main, Germany).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum or plasma are the most widely used sources of sample in clinical routine. The identification of an early tumor marker that would aid in the reliable cancer detection or provide early prognostic information could lead to a method that would greatly aid in the diagnosis and in the management of this disease. Therefore, an urgent clinical need exists to improve the in vitro assessment of cancer and in particular of LC. It is especially important to improve the early diagnosis of cancer, e.g., LC, since for patients diagnosed early on chances of survival are much higher as compared to those diagnosed at a progressed stage of disease.

The clinical utility of biochemical markers in lung cancer has recently been reviewed (Duffy, M. J., Critical Reviews in Clinical Laboratory Sciences 38 (2001) 225-262).

CYFRA 21-1 is currently regarded to be the best of the presently known tumor markers for lung cancer. Even though not organ-specific it is predominantly found in lung tissue. Sensitivity of CYFRA 21-1 for lung cancer is described to be between 46-61% at a specificity of 95% towards other benign lung diseases. Increased serum levels of CYFRA 21-1 are also associated with pronounced benign liver diseases, renal insufficiency and invasive bladder cancer. CYFRA 21-1 testing is recommended for postoperative therapy surveillance.

CEA belongs to the group of carcinofetal antigens, usually produced during embryogenesis. CEA is not organ-specific and predominantly used for monitoring of colorectal cancer. Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. A preferred use of CEA is therapy surveillance of lung cancer.

NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While the sensitivity for SCLC at 95% specificity is reported to be 60-87%, the performance of NSE testing for NSCLC is poor (sensitivity of 7-25%). NSE is recommended for therapy surveillance of SCLC.

With respect to marker profiles and aiming at improved diagnosis of lung cancer, a method was published (Schneider, J., et al., Int. J. Clin. Oncol. 7 (2002) 145-151) using fuzzy logic based classification algorithms to combine serum levels of CYFRA 21-1, NSE and C-reactive protein (CRP) which is a general inflammation marker. The authors report a sensitivity of 92% at a specificity of 95%. However in this study, for example the sensitivity of CYFRA 21-1 as a single tumor marker is reported to be at 72% at a specificity of 95%, which is significantly higher than in many other reported studies. Duffy, M. J., in Critical Reviews in Clinical Laboratory Sciences 38 (2001) 225-262 report a sensitivity of between 46% and 61%. This unusual high performance achieved by Schneider et al., raises some doubts and might be due to several facts. Firstly, the collective of control patients seems to be younger than the patients collective, i.e. the groups are not well age-matched, and the patient collective comprises many late stages. Secondly and even more critical, the performance of the algorithm is checked on the samples of the training set which were used for the determination of the fuzzy logic qualifiers. Hence, these qualifiers are strictly speaking "tailor-made" for this set and not applied to an independent validation set. Under normal circumstances, it has to be expected that the same algorithm applied to a larger, independent, and well balanced validation set will lead to a significantly reduced overall performance.

It was the task of the present invention to investigate whether a biochemical marker can be identified which may be used in assessing cancer disease. In particular, the inventors of the present invention investigated whether a biochemical marker could be identified for the assessment of different cancer types, such as lung, breast, colon, prostate and kidney cancer in body fluids. In a very preferred aspect of the present invention, the identification of a biochemical marker for the assessment of lung cancer (LC) or colorectal cancer (CRC) was investigated.

Surprisingly, it has been found that use of the marker seprase can at least partially overcome some of the problems of the markers presently known in the state of the art.

SUMMARY OF THE INVENTION

The present invention relates to a method for assessing cancer in vitro comprising measuring in a sample the concentration and/or activity of a seprase polypeptide and/or fragments thereof and using the measurement result, particularly the concentration and/or activity determined in the assessment of cancer.

Surprisingly, it was found that a decreased concentration and/or activity of a seprase polypeptide and/or fragments thereof in the test sample is associated with the risk and/or occurrence of cancer. It was further found that seprase is a marker which is not specific for a single type of cancer, but a marker for different types of cancer, i.e., a general tumor marker. Since seprase appears to be rather specific for tumorigenic processes, the novel tumor marker seprase has great potential to be of clinical utility with various classes of tumor types.

The method of the present invention is suitable for the assessment of many different types of cancer. Decreased concentrations and/or activity of seprase or fragments thereof in a sample as compared to normal controls have been found for example in specific cancer types like lung, colon, esophagus, head and neck, stomach, bile duct, pancreas, kidney, cervix, ovary, breast, bladder, endometrium and prostate cancer, respectively.

According to a preferred embodiment of the invention, the concentration and/or activity of seprase is measured in a sample in order to assess specific cancer types, such as lung, colon, esophagus, head and neck, stomach, bile duct, pancreas, kidney, cervix, ovary or breast cancer in vitro.

According to another preferred embodiment of the invention, the concentration and/or activity of seprase is measured in a sample in order to assess cancer, such as lung, colon, esophagus, head and neck, stomach, bile duct, pancreas or kidney cancer in vitro.

According to another preferred embodiment of the invention, the concentration and/or activity of seprase is measured in a sample in order to assess cancer, such as lung, colon, esophagus, head and neck, stomach or bile duct cancer in vitro.

According to another preferred embodiment of the invention, the concentration and/or activity of seprase is measured in a sample in order to assess cancer, such as lung cancer (LC) or colorectal cancer (CRC) in vitro.

According to another preferred embodiment of the invention, the concentration and/or activity of seprase is measured in a sample in order to assess cancer, such as lung cancer (LC) in vitro.

One embodiment of the present invention refers to the mass screening of a population to distinguish between individuals which are probably free from cancer and individuals which might be classified as "suspect" cases. The latter group of individuals could then be subjected to further diagnostic procedures, e.g., by imaging methods or other suitable means.

A further embodiment of the present invention refers to an improvement of tumor marker panels which are suitable for the diagnosis of cancer in general or tumor marker panels which are suitable for the diagnosis of a specific tumor type, e.g., lung cancer or colon cancer.

The present invention is also directed to a method for assessing cancer in vitro by biochemical marker, comprising measuring in a sample the concentration and/or activity of seprase and of one or more other markers specific for cancer, and using the measurement results, particularly concentrations, determined in the assessment of cancer. Preferred markers for use in combination with seprase are, on the one hand, markers which are general tumor markers (i.e, markers which are not specific for a single tumor type) or, on the other hand, specific tumor markers (markers which are specific for a single tumor type). Preferred markers, e.g., for the assessment of cancer, such as lung cancer or colon cancer, are Cyfra 21-1, CEA, NSE, CA19-9, CA125, PSA, ASC, S100A12 and NNMT. These markers may be used individually each or in any combination together with seprase.

If, according to this method of the invention, cancer is assessed, the one or more other marker of the respective cancer is preferably selected from the group consisting of Cyfra 21-1, CEA, NSE, CA19-9, CA125, PSA, ASC, S100A12 and NNMT.

Hence, the present invention, in a preferred embodiment, also relates to the use of a marker panel comprising the marker seprase and at least one other tumor marker, e.g., of Cyfra 21-1, CEA, NSE, CA19-9, CA125, PSA, ASC, S100A12 and NNMT, in the assessment of cancer, e.g., lung and/or colon cancer.

Preferably, the present invention is directed to a method for assessing cancer, such as lung cancer or colon cancer in vitro by biochemical markers, comprising measuring in a sample the concentration and/or activity of seprase and/or fragments thereof and of one or more other cancer markers, e.g., one or more other markers of lung or colon cancer and using the measurement results, particularly concentrations determined in the assessment of cancer. It is preferred that the one or more other marker is selected from the group consisting of Cyfra 21-1, CEA, NSE, CA19-9, CA125, PSA, ASC, S100A12 and NNMT.

The present invention, in a preferred embodiment, also relates to the use of a marker panel comprising at least seprase and CYFRA 21-1 in the assessment of cancer, particularly LC or colon cancer, and more particularly NSCLC or colorectal cancer.

The present invention also relates to the use of a marker panel comprising at least seprase and CEA in the assessment of cancer, particularly LC or colon cancer, and more particularly NSCLC or colorectal cancer.

The present invention also relates to the use of a marker panel comprising at least seprase and SCC in the assessment of cancer, particularly LC or colon cancer, and more particularly NSCLC or colorectal cancer.

The present invention also relates to the use of a seprase polypeptide and/or fragments thereof in the assessment of cancer, wherein a decreased concentration and/or activity of seprase and/or fragments thereof is indicative for cancer.

The present invention also relates to the use of seprase in the assessment of several specific types of cancer, particularly lung, colon, esophagus, head and neck, stomach, bile duct, pancreas, kidney, cervix, ovary, breast, bladder, endometrium or prostate cancer.

The present invention also relates to the use of an antibody directed against a seprase polypeptide and/or fragments thereof in the assessment of cancer, wherein a decreased concentration and/or activity of seprase and/or fragments thereof is indicative for cancer.

The present invention also relates to the use of a reagent for measuring the enzymatic activity of a seprase polypeptide and/or fragments thereof in the assessment of cancer, wherein a decreased concentration and/or activity of seprase and/or fragments thereof is indicative for cancer.

The present invention also provides a kit for performing the method according to the present invention comprising at least the reagents required to specifically measure a seprase polypeptide and/or fragments thereof and one or more other marker of cancer.

The present invention also provides a kit for performing the method according to the present invention comprising at least the reagents required to specifically measure seprase and one or more markers of cancer, e.g., markers of lung, colon, esophagus, head and neck, stomach, bile duct, pancreas, kidney, cervix, ovary, breast, bladder, endometrium or prostate cancer, as described above, wherein the other markers may be each used individually or in any combination thereof.

The present invention also provides a kit for performing the method according to the present invention comprising at least the reagents required to specifically measure seprase and CYFRA 21-1, respectively, and optionally auxiliary reagents for performing the measurement.

The present invention also provides a kit for performing the method according to the present invention comprising at least the reagents required to specifically measure seprase and CEA, respectively, and optionally auxiliary reagents for performing the measurement.

The present invention also provides a kit for performing the method according to the present invention comprising at least the reagents required to specifically measure seprase and SCC, respectively, and optionally auxiliary reagents for performing the measurement.

In a preferred embodiment the present invention relates to a method for assessing cancer in vitro comprising measuring in a sample the concentration and/or activity of (a) a seprase polypeptide and/or fragments thereof, (b) optionally one or more other marker of cancer, and (c) using the measurement result of step (a) and optionally of step (b) in the assessment of cancer, wherein a decreased concentration and/or activity of seprase and/or fragments thereof is indicative for cancer.

BRIEF DESCRIPTION OF THE FIGURES

FIG. 1.

FIG. 2.

FIG. 3.

DETAILED DESCRIPTION OF THE INVENTION

The term "measurement" preferably comprises a qualitative, semi-quantitative or a quantitative measurement of a seprase polypeptide in a sample. In a preferred embodiment the measurement is a semi-quantitative measurement, i.e., it is determined whether the concentration and/or activity of seprase is above or below a cut-off value. As the skilled artisan will appreciate, in a Yes-(presence) or No-(absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. A value below the cut-off value can for example be indicative for the presence of cancer. In particular a value below the cut-off value can for example be indicative for the presence of lung, colon, esophagus, head and neck, stomach, bile duct, pancreas, kidney, cervix, ovary, breast, bladder, endometrium or prostate cancer. In a further preferred embodiment the measurement of seprase is a quantitative measurement. In further embodiments the concentration and/or activity of seprase is correlated to an underlying diagnostic question like, e.g., stage of disease, disease progression, or response to therapy.

Figure 3:
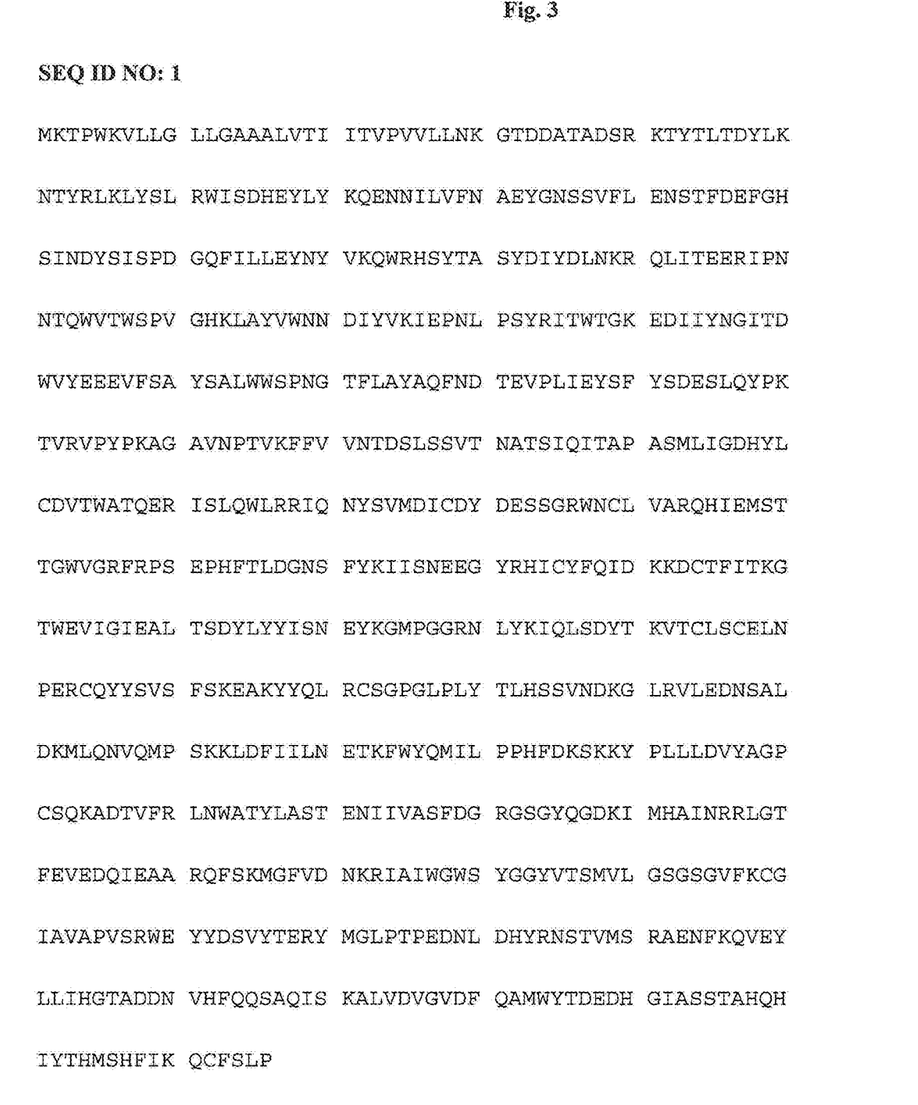
FIG. 3 shows the amino acid sequence of human seprase (SEQ ID NO:1).

Human seprase (alias fibroblast activation protein (FAP)) is a 170 kDa membrane-bound glycoprotein having gelatinase and dipeptidyl peptidase activity, It consists of two identical monomeric units (Uni Prot KB database Accession No. P 27487) characterized by the sequence given in SEQ ID NO:1 (FIG. 3). The seprase monomer comprises 766 amino acids and has an apparent molecular weight of 97 kDa (SDS-PAGE) (Pineiro-Sanchez et al., J. Biol. Chem. 272 (1997) 7595-7601; Park et al., J. Biol. Chem. 274 (1999) 36505-36512). A soluble form of seprase is the antiplasmin-cleaving enzyme APCE (Lee et al., Blood 103 (2004) 3783-3788; Lee et al., Blood 107 (2006) 1397-1404). The N-terminal amino acid sequence of APCE corresponds to residues 24-38 of seprase which is predicted to have its first 6 N-terminal residues within the fibroblast cytoplasm, followed by a 20-residue transmembrane domain and then a 734 residue extracellular C-terminal catalytic domain (Goldstein et al., Biochim. Biophys. Acta. 1361 (1997) 11-19; Scanlan et al., Proc. Natl. Acad. Sci. USA 91 (1994) 5657-5661).

Piñeiro-Sánchez et al. (supra) found that an increased expression of seprase correlates with the invasive phenotype of human melanoma and carcinoma cells. Henry et al, Clin. Cancer Res. 13 (2007) 1736-1741 describe that human colon tumor patients having high levels of stromal seprase are more likely to have aggressive disease progression and potential development of metastases or recurrence.

Hence, none of the above documents of the art suggests that a decreased concentration and/or activity of a seprase polypeptide and/or fragments thereof in body fluids would be indicative for cancer.

Surprisingly, it was found in the present invention that a determination of the concentration and/or the activity, e.g., the enzymatic activity of a seprase polypeptide and/or fragments thereof, particularly of APCE in a body fluid, allows the assessment of cancer, e.g., of lung, colon, esophagus, head and neck, stomach, bile duct, pancreas, kidney, cervix, ovary, breast, bladder, endometrium or prostate cancer. Even more surprisingly, it was found that a decreased concentration and/ or activity of seprase or fragments thereof in a sample compared to normal controls is indicative for the risk or occurrence of cancer.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker. The term "at least" is used to indicate that optionally one or more further objects may be present. By way of example, a marker panel comprising at least (the markers) seprase and CYFRA 21-1 may optionally comprise one or more other marker.

The expression "one or more" denotes 1 to 50, preferably 1 to 20 also preferred 2, 3, 4, 5, 6, 7, 8, 9, 10, 12, or 15.

The term "marker" or "biochemical marker" as used herein refers to a molecule to be used as a target for analyzing a patient's test sample. Examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (=PI) or molecular weight (=MW), or both, e.g., as a result of alternative mRNA or pre-mRNA processing. The amino acid sequence of a variant is to 95% or more identical to the corresponding marker sequence. In addition, or in the alternative a marker polypeptide or a variant thereof may carry a post-translational modification. Non-limiting examples for posttranslational modifications are glycosylation, acylation, and/or phosphorylation.

Seprase:

According to the present invention, the term "seprase polypeptide and/or fragments thereof" refers to monomeric or multimeric, particularly dimeric polypeptides. Further, the term "seprase polypeptide and/or fragments thereof" particularly refers to soluble forms of seprase and/or fragments thereof, particularly antiplasmin-cleaving enzyme (APCE) as well as to seprase and/or seprase fragments present in form of a complex with another polypeptide.

Seprase polypeptides, particularly soluble forms of seprase polypeptides and/or fragments thereof, are preferably detected in appropriate samples, particularly body fluids. Preferred samples are body fluids, such as blood, plasma, serum, sputum, urine, feces etc. Preferably, the sample is derived from a human subject, e.g., a tumor patient or a person in risk of a tumor or a person suspected of having a tumor.

According to the present invention, the concentration and/ or activity of a seprase polypeptide and/or fragments thereof is determined. In one embodiment, the marker seprase is specifically measured from a sample by use of a specific binding agent.

A specific binding agent is, e.g., a receptor for seprase, a lectin binding to seprase or an antibody to seprase. A specific binding agent has at least an affinity of $10^7$ l/mol for its corresponding target molecule. The specific binding agent preferably has an affinity of $10^8$ l/mol or also preferred of $10^8$ l/mol for its target molecule. As the skilled artisan will appreciate the term specific is used to indicate that other biomolecules present in the sample do not significantly bind to the binding agent specific for seprase. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity.

A specific binding agent preferably is an antibody reactive with seprase. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen, P., Practice and theory of enzyme immunoassays, 11, Elsevier Science Publishers B. V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in rabbits may be used. However, clearly also polyclonal antibodies from different species, e.g., rats or guinea pigs, as well as monoclonal antibodies can also be used. Since monoclonal antibodies can be produced in any amount required with constant properties, they represent ideal tools in development of an assay for clinical routine. The generation and the use of monoclonal antibodies to seprase in a method according to the present invention, respectively, represent yet other preferred embodiments. Preferred examples of antibodies suitable for the detection of seprase are disclosed in Piñeiro-Sánchez et al., supra, e.g., the antibodies D8, D28 and D43.

As the skilled artisan will appreciate now that seprase has been identified as a marker which is useful in the assessment of cancer, preferably of lung or colon cancer. Various immunodiagnostic procedures may be used to reach a result comparable to the achievements of the present invention. For example, alternative strategies to generate antibodies may be used. Such strategies comprise amongst others the use of synthetic peptides, representing an epitope of seprase for immunization. Alternatively, DNA immunization also known as DNA vaccination may be used.

For measurement the sample obtained from an individual is incubated with the specific binding agent for seprase under conditions appropriate for formation of a binding agent seprase complex. Such conditions need not be specified, since the skilled artisan without any inventive effort can easily identify such appropriate incubation conditions. The amount of binding agent seprase complex is measured and used in the assessment of cancer, preferably of lung cancer. As the skilled artisan will appreciate there are numerous methods to measure the amount of the specific binding agent seprase complex all described in detail in relevant textbooks (cf., e.g., Tijssen, P., supra, or Diamandis, E. P., and Christopoulos, T. K. (eds.), Immunoassay, Academic Press, Boston (1996)).

Preferably, seprase is detected in a sandwich-type assay format. In such assay, a first specific binding agent is used to capture seprase on the one side and a second specific binding agent, which is labelled to be directly or indirectly detectable, is used on the other side. The specific binding agents used in a sandwich-type assay format may be antibodies specifically directed against seprase. On the one hand, the detection may be carried out by using different capturing and labelled antibodies, i.e., antibodies which recognize different epitopes on the seprase polypeptide. On the other hand, a sandwich-type assay may also be carried out with a capture and labelling antibody which is directed against the same epitope of seprase. In this embodiment, only di- and multimeric forms of seprase may be detected.

According to a further embodiment of the invention, the marker seprase is specifically measured from a sample by use of a test regimen suitable for detecting the enzymatic activity of seprase. The enzymatic activity may, e.g., be a gelatinase activity or a peptidase activity. Gelatinase activity may, e.g., be determined by zymography using gelatine zymograms. Peptidase activity may, e.g., be determined by fluorescent assays using peptide substrates. Assays for the measurement of seprase activity are, e.g., described by Lee et al. (2006), supra.

A "marker of cancer" and in particular a "marker of lung cancer" and "marker of colon cancer" in the sense of the present invention is any marker that if combined with the marker seprase adds relevant information in the assessment of cancer, e.g in the assessment of cancer in general or in the assessment of certain cancer types, e.g., in the assessment of LC or CRC. The information is considered relevant or of additive value if at a given specificity the sensitivity, or if at a given sensitivity the specificity, respectively, for the assessment of cancer can be improved by including said marker into a marker combination already comprising the marker seprase. In the preferred embodiment of cancer assessment, the improvement in sensitivity or specificity, respectively, is statistically significant at a level of significance of $p=0.05$, 0.02, 0.01 or lower. Preferably, the one or more other tumor marker is selected from the group consisting of CYFRA 21-1, CEA, NSE, CA 19-9, CA 125, PSA, ASC, S100A12 and NNMT.

The term "sample" as used herein refers to a biological sample obtained for the purpose of evaluation in vitro. In the methods of the present invention, the sample or patient sample preferably may comprise any body fluid. Preferred samples are whole blood, serum, plasma, bronchial lavage or sputum, with plasma or serum being most preferred.

The term "assessing cancer" and in particular "assessing lung cancer" or "assessing colon cancer" is used to indicate that the method according to the present invention will (alone or together with other markers or variables, e.g., the criteria set forth by the UICC (see above), e.g., aid the physician to establish or confirm the absence or presence of cancer, in particular of LC or of CRC or aid the physician in the prognosis, the detection of recurrence (follow-up of patients after surgery) and/or the monitoring of treatment, especially of chemotherapy.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

In a preferred embodiment the present invention relates to a method for assessing cancer, e.g., LC or CRC, in vitro by biochemical markers, comprising measuring in a sample the concentration of seprase and using the concentration and/or activity determined in the assessment of cancer, e.g., LC or CRC.

The inventors of the present invention have surprisingly been able to detect a decreased concentration and/or activity of the marker seprase in a significant percentage of samples derived from patients with cancer, in particular with lung, colon, esophagus, head and neck, stomach, bile duct, pancreas, kidney, cervix, ovary, breast, bladder, endometrium or prostate cancer. Even more surprising they have been able to demonstrate that the decreased concentration and/or activity of seprase in such sample obtained from an individual can be used in the assessment of cancer, in particular of the above-mentioned cancer diseases.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for many cancer types, e.g., for LC. As the skilled artisan will appreciate, no biochemical marker is diagnostic with 100% specificity and at the same time 100% sensitivity for a given multifactorial disease, for example for LC. Rather, biochemical markers, e.g., CYFRA 21-1, CEA, NSE, or as shown here seprase can be used to assess with a certain likelihood or predictive value, e.g., the presence, absence, or the severity of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then either interpreted independently, e.g., using an individual cut-off for each marker, or they are combined for interpretation.

In a further preferred embodiment the assessment of cancer according to the present invention is performed in a method comprising measuring in a sample the concentration and/or activity of a) a seprase polypeptide and/or fragments thereof, and b) one or more other marker of cancer, and c) using the measurement result, e.g., the concentrations determined in step (a) and step (b), respectively, in the assessment of cancer.

In the assessment of cancer the marker seprase will be of advantage in one or more of the following aspects: screening; diagnostic aid; prognosis; monitoring of therapy such as chemotherapy, radiotherapy, and immunotherapy.

Screening:

Screening is defined as the systematic application of a test to identify individuals, e.g., at risk individuals, for indicators of a disease, e.g., the presence of cancer. Preferably the screening population is composed of individuals known to be at higher than average risk of cancer. For example, a screening population for lung cancer is composed of individuals known to be at higher than average risk of lung cancer, like smokers, ex-smokers, and uranium-, quartz- or asbestos-exposed workers.

In the preferred embodiment, a body fluid such as serum or sputum, is used as a sample in the screening for cancer, e.g., lung or colorectal cancer.

For many diseases, no single biochemical marker in the circulation will ever meet the sensitivity and specificity criteria required for screening purposes. This appears to be also true for cancer and in particular for lung cancer. It has to be expected that a marker panel comprising a plurality of markers will have to be used in cancer screening. The data established in the present invention indicate that the marker seprase will form an integral part of a marker panel appropriate for screening purposes. The present invention therefore relates to the use of seprase as one marker of a cancer marker panel, i.e., a marker panel comprising seprase and one or more additional marker for cancer screening purposes. In particular, the present invention relates to the use of seprase as one marker of a general cancer marker panel. Such marker panel comprises the marker seprase and one or more additional markers, e.g., general cancer markers and/or markers for the above-mentioned type of cancer.

Seprase is also likely to contribute to marker panels for certain specific types of cancer, e.g., lung, colon, esophagus, head and neck, stomach, bile duct, pancreas, kidney, cervix, ovary, breast, bladder, endometrium or prostate cancer.

Other preferred types of cancer to be assessed with a marker panel comprising seprase are lung, colon, esophagus, head and neck, stomach, bile duct, pancreas or kidney cancer.

Other preferred types of cancer to be assessed with a marker panel comprising seprase are lung, colon, esophagus, head and neck, stomach or bile duct cancer.

Other preferred types of cancer to be assessed with a marker panel comprising seprase are lung cancer or colon cancer.

A preferred type of cancer to be assessed with a marker panel comprising seprase is lung cancer (LC).

The present data further indicate that certain combinations of markers will be advantageous in the screening for cancer. For example, with reference to the preferred embodiment of screening LC or CRC, the present invention also relates to the use of a marker panel comprising seprase and CYFRA 21-1, or of a marker panel comprising seprase and CEA, or of a marker panel comprising seprase and NSE, or of a marker panel comprising seprase and CA 19-9, or of a marker panel comprising seprase and CA 125, or of a marker panel comprising seprase and PSA, or of a marker panel comprising seprase and ASC, or of a marker panel comprising seprase and S100A12, or of a marker panel comprising seprase and NNMT, or of a marker panel comprising seprase and two or more markers selected from the group consisting of CYFRA 21-1, CEA, NSE, CA 19-9, CA 125, PSA, ASC, S100A12 and NNMT.

Diagnostic Aid:

Markers may either aid the differential diagnosis of benign vs. malignant disease in a particular organ, help to distinguish between different histological types of a tumor, or to establish baseline marker values before surgery.

Today, important methods used in the detection of cancer are radiology and/or computed tomography (CT) scans. Small nodules, i.e., small regions of suspect tissue can be visualized by these methods. However, many of these nodules—more than 90% with CT—represent benign tissues changes, and only a minority of nodules represents cancerous tissue. Use of the marker seprase may aid in the differentiation of benign versus malign disease.

Since seprase as a single marker might be superior to other markers, e.g., in the case of LC to other markers, like CEA or NSE, it has to be expected that seprase will be used as a diagnostic aid, especially by establishing a baseline value before surgery. The present invention thus also relates to the use of seprase for establishing a baseline value before surgery for cancer.

Prognosis:

Prognostic indicators can be defined as clinical, pathological, or biochemical features of cancer patients and their tumors that predict with a certain likelihood the disease outcome. Their main use is to help to rationally plan patient management, i.e., to avoid undertreatment of aggressive disease and overtreatment of indolent disease, respectively. Molina, R., et al., Tumor Biol. 24 (2003) 209-218 evaluated the prognostic value of CEA, CA 125, CYFRA 21-1, SSC and NSE, in NSCLC. In their study abnormal serum levels of the markers NSE, CEA, and LDH (lactate dehydrogenase) appeared to indicate shorter survival.

As seprase alone significantly contributes to the differentiation of cancer patients, e.g., LC or CRC patients, from healthy controls, it has to be expected that it will aid in assessing the prognosis of patients suffering from cancer, preferably from LC or CRC. The level of preoperative seprase will most likely be combined with one or more other marker for cancer and/or the TNM staging system. In a preferred embodiment seprase is used in the prognosis of patients with LC or CRC.

Monitoring of Chemotherapy:

Merle, P., et al., Int. J. of Biological Markers 19 (2004) 310-315 have evaluated CYFRA 21-1 serum level variations in patients with locally advanced NSCLC treated with induction chemotherapy. They conclude that early monitoring of CYFRA 21-1 serum levels may be a useful prognostic tool for tumor response and survival in stage III NSCLC patients, In addition, reports have described the use of CEA in monitoring the treatment of patients with LC (Fukasawa, T., et al., Cancer & Chemotherapy 13 (1986) 1862-1867). Most of these studies were retrospective, non-randomized and contained small numbers of patients. As in the case of the studies with CYFRA 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

It is expected that seprase will be at least as good a marker for monitoring of chemotherapy as CYFRA 21-1 or CEA, respectively. The present invention therefore also relates to the use of seprase in the monitoring of cancer patients and preferably of lung cancer (LC) or colon cancer (CRC) patients under chemotherapy. In the monitoring of therapy in one preferred embodiment the measurements for seprase and for at least one marker selected from the group consisting of CYFRA 21-1, CEA and/or NSE will be combined and used in the assessment of lung (LC) cancer.

Follow-Up:

A large portion of LC patients who undergo surgical resection aimed at complete removal of cancerous tissue later develop recurrent or metastatic disease (Wagner, H., Chest 117 (2000) 110-118; Buccheri, G., et al., Ann. Thorac. Surg. 75 (2003) 973-980). Most of these relapses occur within the first 2-3 years after surgery. Since recurrent/metastatic disease is invariably fatal if detected too late, considerable research has focused on cancer relapse at an early and thus potentially treatable stage.

Consequently, many cancer patients, e.g., LC patients undergo a postoperative surveillance program which frequently includes regular monitoring with CEA. Serial monitoring with CEA one year after surgical resection has been shown to detect an early postoperative recurrent/metastatic disease with a sensitivity of approximately 29%, at a specificity of approximately 97%, even in the absence of suspicious symptoms or signs (Buccheri, G., et al., Ann. Thorac. Surg. 75 (2003) 973-980). Thus, the follow-up of patients with LC after surgery is one of the most important fields of use for an appropriate biochemical marker. Due to the high sensitivity of seprase in the LC patients investigated it is likely that seprase alone or in combination with one or more other marker will be of great help in the follow-up of LC patients, especially in LC patients after surgery. The use of a marker panel comprising seprase and one or more other marker of LC in the follow-up of LC patients represents a further preferred embodiment of the present invention.

The present invention in a preferred embodiment relates to the use of seprase in the diagnostic field of cancer. Preferably seprase is used in the assessment of lung (LC), colon (CRC), esophagus, head and neck, stomach, bile duct, pancreas, kidney, cervix, ovary, breast, bladder, endometrium or prostate cancer, respectively.

In yet a further preferred embodiment the present invention relates to the use of seprase as a marker molecule for cancer, e.g., for cancer in general or for specific types of cancer, such as lung, colon, esophagus, head and neck, stomach, bile duct, pancreas, kidney, cervix, ovary, breast, bladder, endometrium or prostate cancer in combination with one or more further marker molecules for cancer. The further marker molecules may be cancer-type unspecific general marker molecules and/or cancer-type specific marker molecules, e.g., marker molecules for lung or colon cancer. Seprase and the at least one further marker are used in the assessment of cancer, e.g., lung or colon cancer in a liquid sample obtained from an individual. Preferred selected other cancer markers with which the measurement of seprase may be combined are Cyfra 21-1, CEA, NSE, CA125, CA19-9, PSA, ASC, S100A12 and NNMT. In particular, preferred selected other LC markers with which the measurement of seprase may be combined are CYFRA 21-1, CEA and/or NSE. Yet further preferred the marker panel used in the assessment of cancer, e.g., LC comprises seprase and at least one other marker molecule selected from the group consisting of CYFRA 21-1 and CEA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may, e.g., the case when diagnosing an infectious disease, like AIDS.

Frequently, however, the combination of markers is evaluated. Preferably the values measured for markers of a marker panel, e.g., for seprase and CYFRA 21-1, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention, e.g., to the absence or presence of LC is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., et al, J. of Computational and Graphical Statistics, 12 (2003) 475-511; Friedman, J. H., J. of the American Statistical Association 84 (1989) 165-175; Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. (1984) Classification and regression trees, California: Wadsworth; Breiman, L., Random Forests, Machine Learning, 45 (2001) 5-32; Pepe, M. S., The Statistical Evaluation of Medical Tests for Classification and Prediction, Oxford Statistical Science Series 28 (2003);

and Duda, R. O., Hart, P. E., Stork, D. G., Pattern Classification, Wiley Interscience, 2nd Edition (2001).

It is a preferred embodiment of the invention to use an optimized multivariate cut-off for the underlying combination of biological markers and to discriminate state A from state B, e.g., diseased from healthy. In this type of analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision threshold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1−specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One preferred way to quantify the diagnostic accuracy of a laboratory test is to express its performance by a single number. Such an overall parameter, e.g., is the so-called "total error" or alternatively the "area under the curve=AUC". The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In a preferred embodiment the present invention relates to a method for improving the diagnostic accuracy for cancer, e.g., LC or CRC versus healthy controls by measuring in a sample the concentration of at least seprase and CYFRA 21-1, and optionally of CEA, and/or NSE, respectively and correlating the concentrations determined to the presence or absence of cancer, e.g., LC or CRC, the improvement resulting in more patients being correctly classified as suffering from cancer, e.g., LC or CRC versus healthy controls as compared to a classification based on any single marker investigated alone.

In a preferred method according to the present invention at least the concentration of the biomarkers seprase and CYFRA 21-1, respectively, is determined and the marker combination is used in the assessment of cancer, e.g., LC or CRC.

In a further preferred method according to the present invention at least the concentration of the biomarkers seprase and CEA, respectively, is determined and the marker combination is used in the assessment of cancer, e.g., LC or CRC.

In a further preferred method according to the present invention at least the concentration of the biomarkers seprase, CYFRA 21-1, and CEA, respectively, is determined and the marker combination is used in the assessment of cancer, e.g., LC or CRC.

In a further preferred method according to the present invention at least the concentration of the biomarkers seprase, CYFRA 21-1, and CEA, respectively, is determined and the marker combination is used in the assessment of cancer, e.g., LC or CRC.

In yet a further preferred method according to the present invention at least the concentration of the biomarkers seprase, CYFRA 21-1, and NSE, respectively, is determined and the marker combination is used in the assessment of cancer, e.g., LC or CRC.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

As seprase-specific binding molecules rat monoclonal anti-seprase antibodies (clones D8, D28 and D43) were used (Pineiro-Sanchez, M.-L., et al., J. Biol. Chem., 272 (1997) 7595-7601).

Biotinylation of Monoclonal Rat IgG

Monoclonal rat IgG (clones D28 or D43) was brought to 10 mg/ml in 10 mM $NaH_2PO_4$/NaOH, pH 7.5, 30 mM NaCl. Per ml IgG solution 50 µl Biotin —N-hydroxysuccinimide (3.6 mg/ml in DMSO) were added. After 30 min at room temperature, the sample was chromatographed on Superdex 200 (10 mM $NaH_2PO_4$/NaOH, pH 7.5, 30 mM NaCl). The fraction containing biotinylated IgG were collected.

Digoxygenylation of Monoclonal Rat IgG

Monoclonal rat IgG (clones D8 or D43) was brought to 10 mg/ml in 10 mM $NaH_2PO_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) were added. After 30 mM at room temperature, the sample was chromatographed on Superdex® 200 (10 mM $NaH_2PO_4$/NaOH, pH 7.5, 30 mM NaCl). The fractions containing digoxigenylated IgG were collected.

EXAMPLE 2

ELISA for the measurement of seprase in human serum and plasma samples.

For detection of seprase in human serum or plasma, a sandwich ELISA was developed. In a first assay format, aliquots of the anti-seprase monoclonal antibodies D28 conjugated with biotin and D8 conjugated with digoxigenin (see Example 1) were used for capture and detection of the antigen (D28×D8 format). In a second assay format, aliquots of the anti-seprase monoclonal antibody D43 (see Example 1) conjugated with biotin and digoxigenin, respectively, were used for capture and detection of the antigen (D43×D43 format).

Samples (75 µl) were mixed with 150 µl of antibody reagent containing 0.375 µg of each, D28-biotin and D8-digoxigenin antibodies or alternatively D43-biotin and D43-digoxigenin antibodies in incubation buffer (40 mM phosphate, 200 mM sodium tartrate, 10 mM EDTA, 0.05% phenol, 0.1% polyethylene glycol 40000, 0.1% Tween 20, 0.2% BSA, 0.1% bovine IgG, and 0.02% 5-Bromo-5-Nitro-1,3-Dioxane and adjusted to pH 7.4).

After incubation for two hours, 2×100 µl of the mixture was transferred into separate wells of a streptavidin-coated microtiter plate and incubated for another hour. Plates were washed three times with washing buffer (10 mM Tris, 150 mM NaCl, 0.05% Tween 20).

In a next step, wells were incubated with 30 mU/ml anti-digoxigenin-HRP conjugate (Roche Diagnostics GmbH, Mannheim, Germany, Catalog #1633716) in Universal Conjugate Buffer (Roche Diagnostics GmbH, Mannheim, Germany, Catalog #11684825) for 60 min and washed as before.

Wells were then incubated for 1 hour with 100 µl of TMB substrate solution (Roche Diagnostics GmbH, Mannheim, Germany, Catalog #12034425). Adding of 2N sulfuric acid (50 µl) stopped the color development and switched the blue color into yellow.

OD was measured at 450 nm with an ELISA reader.

All incubations were at room temperature. Samples of human serum or plasma were pre-diluted with incubation buffer ad 0.15%. For calibration, a serum pool was used as a standard. It was diluted with incubation buffer ad 0.09/0.18/0.27/0.36/0.45% to make calibrators with arbitrarily given values of 0.03/0.06/0.09/0.12/0.15 Units/ml, respectively.

The equation of the calibration curve was calculated by linear regression analysis and used for converting the absorbance reading of a well into the corresponding concentration value. The result was multiplied by the pre-dilution factor to get the concentration of the respective sample itself.

EXAMPLE 3

CRC Study Population

In a first study, samples derived from 49 well-characterized patients with colorectal cancer (UICC classification given in Table 1) have been used.

TABLE 1

| CRC study: distribution of samples across UICC stages | |
| --- | --- |
| Stage according to UICC | Number of samples |
| UICC I | 8 |
| UICC II | 8 |
| UICC III | 15 |
| UICC IV | 4 |
| without staging | 14 |
| total number of CRC samples | 49 |

The samples of Table 1 have been evaluated in comparison with control samples obtained from 50 obviously healthy individuals without any known malignant disease (=control cohort).

EXAMPLE 4

LC Study Population

A second study totally independent from the first one focused on non small cell lung cancer (NSCLC). More specifically, patients suffering from the main types of NSCL, adenocarcinoma and squamous cell carcinoma were investigated. Table 2a describes the type and stage distribution of the cancer cohort.

TABLE 2a

| LC study: Type and staging of LC samples | | |
| --- | --- | --- |
| | Number of samples | |
| Type of Cancer | UICC I or II | UICC III or IV |
| Adenocarcinoma | 12 | 18 |
| Squamous cell carcinoma | 12 | 18 |
| total number of NSCLC samples | 60 | |

The control cohort in this study was defined especially to comprise samples from smokers and non-smokers as described in Table 2b. A spirometry lung function testing (Miller, M. R. et al., Eur. Respir. J. 26 (2005) 319-338) was carried out with each individual. Samples were included in the control cohort only if the donor's result was within the normal range.

TABLE 2b

| LC study: Composition of the control cohort | |
| --- | --- |
| Stage according to UICC | Number of samples |
| Smokers | 30 |
| Ex-smokers | 6 |
| Non-smokers | 24 |

EXAMPLE 5

Seprase Discriminates Cancer Patients from Healthy Controls

Figure 1:
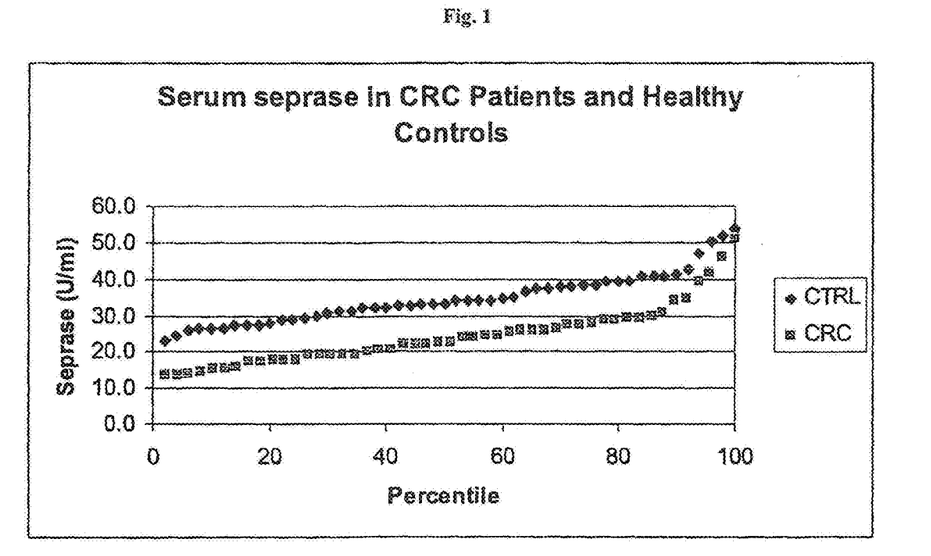
FIG. 1 shows the distribution of serum seprase concentration values in colorectal cancer (CRC) patients and healthy control patients and healthy controls.
Figure 2:
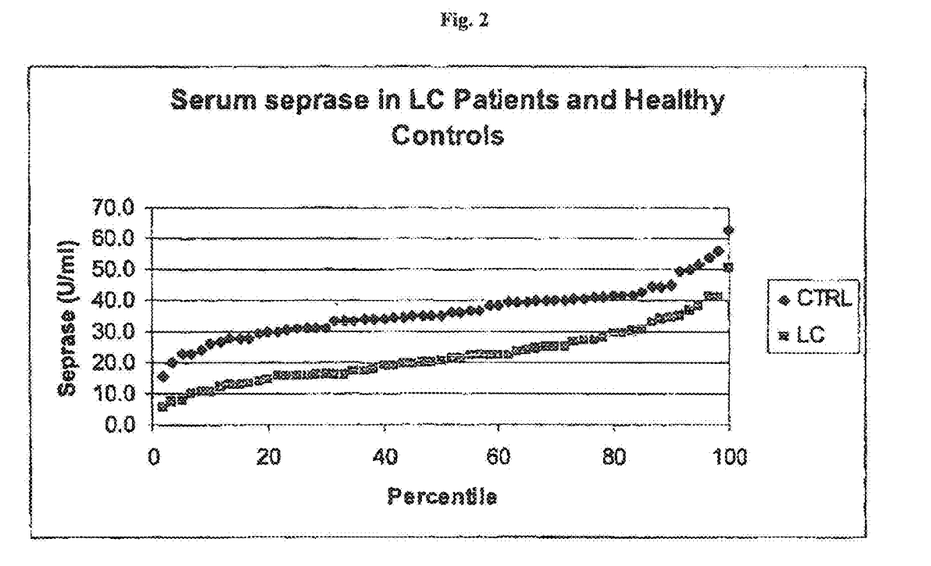
FIG. 2 shows the distribution of serum seprase concentration values in lung cancer (LC) patients and healthy controls.

The serum concentration of seprase differs markedly between cancer patients and healthy controls, as was found in both studies. In FIGS. 1 and 2, the results of an assay using a combination of D28 and D8 antibodies is shown.

The mean concentration of the cancer patient cohorts is significantly lower than that of the control cohorts: 22.6 and 20.9 U/ml in patients vs. 33.6 and 35.6 U/ml in controls was found in the CRC and the LC study, respectively. With a cut-off value that yields 95% specificity on the respective control cohort, the sensitivity for colorectal cancer is 67%. For lung cancer it is 62%.

The sensitivity is similar for all stages of cancer, as can be seen from both, the CRC and LC data (Tables 3 and 4). Therefore, seprase can be used as an early indicator of disease. With respect to lung cancer, the sensitivity for squamous cell carcinoma is higher than for adenocarcinoma (Table 4).

TABLE 3

CRC study: sensitivity depending on UICC classification

| Stage according to UICC | Number of samples | Number positive | % positive |
|---|---|---|---|
| UICC I | 8 | 6 | 75 |
| UICC II | 8 | 4 | 50 |
| UICC III | 15 | 11 | 73 |
| UICC IV | 4 | 3 | 75 |
| without staging | 14 | 9 | 64 |
| total number of CRC samples | 49 | 33 | 67 |

TABLE 4

LC study: sensitivity depending on type and staging

| Stage and type of LC | Number of samples | Number positive | % positive |
|---|---|---|---|
| UICC I and II | 24 | 15 | 63 |
| UICC III and IV | 36 | 22 | 61 |
| Adenocarcinoma | 30 | 15 | 50 |
| Squamous cell carcinoma | 30 | 22 | 73 |
| total number of LC samples | 60 | 37 | 62 |

The results of assays using two D43 antibodies which detect only dimeric or multimeric forms of seprase were closely correlated thereto (data not shown).

EXAMPLE 6

Sensitivity of Other Markers for CRC and LC

Besides seprase, we determined ten other well-known tumor markers in the CRC and LC study samples. Commercially available test kits were used in this case. To make a fair comparison between them, the cut off value of each marker investigated was set as to yield 95% specificity on the control cohort of the respective study.

Table 5 presents the sensitivity of each marker for the detection of both cancer types.

TABLE 5

Sensitivity of various cancer markers for CRC and LC

| Marker | Sensitivity (%) for colorectal cancer | Sensitivity (%) for lung cancer | Mean |
|---|---|---|---|
| Seprase | 67 | 62 | 64.5 |
| CEA | 33 | 32 | 32.5 |
| NSE | 15 | 35 | 25 |
| CA 15-3 | 10 | 20 | 15 |
| CA 72-4 | 21 | 7 | 14 |
| CYFRA 21-1 | 57 | 72 | 64.5 |
| S100 | 16 | 22 | 19 |
| AFP | 10 | 7 | 8.5 |
| hCG-β | 9 | 8 | 8.5 |
| CA 19-9 | 31 | 18 | 24.5 |
| CA 125 | 16 | 32 | 24 |

Seprase demonstrates similar sensitivity for CRC and LC. Overall, it averages at 64.5%, the highest value observed among all the markers assessed. Only Cyfra 21-1 has the same mean sensitivity. However, Cyfra is significantly less effective in the detection of CRC than seprase. The performance shown by all the other tumor markers measured is rather poor compared with these both.

EXAMPLE 7

Marker Combinations

An individual was classified as having cancer if at least one of the markers of the respective combination exceeds a certain threshold. In general, these cut-off values were different from the ones used for the single marker case, but analogously yielded 95% specificity with the respective combination.

The combination of the two most prominent markers, seprase and Cyfra 21-1, markedly improved the detection of cancer and gave 80% sensitivity in the LC study.

EXAMPLE 8

Discrimination of Different Cancers from Age-Matched Healthy Controls Using Seprase as Tumor Marker In this study samples from well-characterized patients with different cancer diseases (sample numbers and UICC classification is given in table 6) were measured. The samples of table 6 were evaluated in comparison to 264 age-matched control patients, which were obviously healthy individuals without any known malignant disease. In this control cohort the cut-off was determined to obtain a specificity of 95%.

TABLE 6

Sensitivity of Seprase in different cancer entities

| Cancer entity | Sample number | UICC 0 | UICC I | UICC II | UICC III | UICC IV | UICC unknown | Sensitivity (%) |
|---|---|---|---|---|---|---|---|---|
| Bile duct | 10 | — | — | 3 | 1 | 6 | — | 50 |
| Bladder | 8 | — | — | 2 | 5 | 1 | — | 13 |
| Breast | 44 | — | 19 | 18 | 6 | 1 | — | 18 |
| Cervix | 16 | — | 6 | 1 | 7 | 2 | — | 25 |
| Endometrium | 15 | 1 | 9 | 2 | 2 | 1 | — | 13 |
| Esophagus | 30 | — | 5 | 3 | 12 | 4 | 6 | 70 |
| Head/Neck | 30 | — | 2 | 2 | 3 | 21 | 2 | 60 |
| Kidney | 23 | — | 4 | — | 2 | 5 | 12 | 39 |
| Ovary | 23 | — | 3 | 1 | 9 | 8 | 2 | 22 |
| Pancreas | 64 | — | 2 | 26 | 5 | 22 | 9 | 45 |
| Prostate | 33 | — | — | 25 | 4 | 3 | 1 | 6 |
| Stomach | 37 | — | 8 | 8 | 6 | 13 | 2 | 54 |

High sensitivities for seprase were obtained in esophagus, head/neck, stomach and bile duct cancer, as well as for LC and CRC (data shown in Table 5). Good sensitivity for seprase has also been found for Pancreas and Kidney cancer. Less sensitivity has been found for seprase in the assessment of cervix, ovary and breast cancer. In spite of a comparatively low sensitivity in breast cancer (18%) in a screening setting (at 95% specificity), seprase can also be considered as an interesting marker for recurrence monitoring of breast cancer. The markers CA 15-3 and CEA, which are routinely used for this intended use showed only a sensitivity of 6% and 11%, respectively, in this breast cancer collective, which is less as compared to the marker seprase.

What is claimed is:

1. A method for providing a diagnosis of cancer in a subject suspected of having at least one of lung cancer, colon cancer, esophageal cancer, head and neck cancer, stomach cancer, bile duct cancer, pancreatic cancer, kidney cancer, cervical cancer, ovarian cancer, breast cancer, bladder cancer, endometrial cancer and prostate cancer, comprising:
contacting, in vitro, a portion of a sample selected from the group consisting of serum and plasma from a subject with a specific binding agent, wherein the specific binding agent is selected from the group consisting of an antibody, a receptor, a lectin and a nucleic acid and has specific binding affinity for a seprase marker, wherein the specific binding agent and the seprase marker form a binding agent seprase marker complex;
detecting the binding agent seprase marker complex formed, thereby determining an amount of the seprase marker;
comparing the amount of the seprase marker to a control value, wherein the control value is an amount of the seprase marker from a control cohort; and
providing a diagnosis of cancer if the amount of the seprase marker is significantly less than the control value based on said step of comparing.

2. The method of claim 1, wherein the specific agent comprises an antibody.

3. The method of claim 1, further comprising the steps of:
contacting, in vitro, a portion of the sample from the subject with a specific binding agent having specific binding affinity for a marker selected from the group consisting of a cytokeratin 19 fragment (CYFRA 21-1) marker, a carcinoembryogenic antigen (CEA) marker, a neuron-specific enolase (NSE) marker, a CA 19-9 marker, a CA125 marker, a PSA marker, a ASC marker, a S100A12 marker and a NNMT marker; and
detecting the complex formed, thereby determining an amount of the marker selected from the group consisting of the CYFRA 21-1 marker, the carcinoembryogenic antigen (CEA) marker, the neuron-specific enolase (NSE) marker, the CA 19-9 marker, the CA125 marker, the PSA marker, the ASC marker, the S100A12 marker and the NNMT marker.

4. The method of claim 3, further comprising the step of comparing the amount of the CYFRA 21-1 marker to a CYFRA 21-1 control value, wherein the control value is an amount of the CYFRA 21-1 marker from a control cohort, and wherein said step of providing a diagnosis of cancer further comprises the amount of the CYFRA 21-1 marker being greater than the control value.

5. The method of claim 1, wherein a diagnosis of cancer is provided, further comprising the step of treating the subject with one of chemotherapy, surgical resection, and anti-tumor antibodies.

6. A method for providing a diagnosis of cancer in a subject suspected of having colorectal cancer, comprising:
contacting, in vitro, a portion of a sample selected from the group consisting of serum and plasma from the subject with a specific binding agent, wherein the specific binding agent is selected from the group consisting of an antibody, a receptor, a lectin and a nucleic acid and has specific binding affinity for a seprase marker, wherein the specific binding agent and the seprase marker form a binding agent seprase marker complex;
detecting the binding agent seprase marker complex formed, thereby determining an amount of the seprase marker; and
providing a diagnosis of colorectal cancer if the amount of the seprase marker is significantly less than a control value, wherein the control value is an amount of the seprase marker from a control cohort.

7. The method of claim 6, further comprising the steps of:
contacting, in vitro, a portion of the sample from the subject with a specific binding agent having specific binding affinity for a CYFRA 21-1 marker; and
detecting the binding agent CYFRA 21-1 marker complex formed, thereby determining an amount of the CYFRA 21-1 marker, wherein said step of providing a diagnosis of cancer further comprises the amount of the CYFRA 21-1 marker being greater than a CYFRA 21-1 control value, wherein the control value is an amount of the CYFRA 21-1 marker from a control cohort.

8. The method of claim 6, wherein the amount of the seprase marker from the subject is about 1.5-fold less than the amount of the seprase marker from the control cohort.

9. The method of claim 6 further comprising subjecting the subject to at least one additional cancer diagnostic procedure.

10. The method of claim 9, wherein the further diagnostic procedure is selected from the group consisting of: an x-ray and a nuclear resonance imaging.

11. The method of claim 6 further comprising subjecting the subject to at least one additional cancer diagnostic procedure.

12. The method of claim 11, wherein the further diagnostic procedure is selected from the group consisting of: an x-ray and a nuclear resonance imaging.

13. A method for providing a diagnosis of cancer in a subject suspected of having lung cancer, comprising:
contacting, in vitro, a portion of a sample selected from the group consisting of serum and plasma from the subject with a specific binding agent, wherein the specific binding agent is selected from the group consisting of an antibody, a receptor, a lectin and a nucleic acid and has specific binding affinity for a seprase marker, wherein the specific binding agent and the seprase marker form a binding agent seprase marker complex;
detecting the binding agent seprase marker complex formed, thereby determining an amount of the seprase marker;
comparing the amount of the seprase marker to a control value, wherein the control value is an amount of the seprase marker from a control cohort; and
providing a diagnosis of lung cancer if the amount of the seprase marker is significantly less than the control value based on said step of comparing.

14. The method of claim 13, further comprising the step of contacting, in vitro, a portion of the sample from the subject with a specific binding agent having specific binding affinity for a marker selected from the group consisting of a CYFRA 21-1 marker, detecting the binding agent CYFRA 21-1 marker complex formed, thereby determining an amount of the CYFRA 21-1 marker, and comparing the amount of the CYFRA 21-1 marker with a CYFRA 21-1 control value, wherein the control value is an amount of the CYFRA 21-1 marker from a control cohort.

15. The method of claim 13, wherein the amount of the seprase marker from the subject is about 1.5-fold less than the amount of the seprase marker from the control cohort.

\* \* \* \* \*

SEQUENCE LISTING

```
<160> NUMBER OF SEQ ID NOS: 1

<210> SEQ ID NO 1
<211> LENGTH: 766
<212> TYPE: PRT
<213> ORGANISM: Homo sapiens

<400> SEQUENCE: 1

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320
```

```
Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735
```

```
Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765
```